United States Patent
Cho et al.

(10) Patent No.: US 10,434,067 B2
(45) Date of Patent: Oct. 8, 2019

(54) COMPOSITE FORMULATION FOR ORAL ADMINISTRATION COMPRISING EZETIMIBE AND ROSUVASTATIN

(71) Applicant: HANMI PHARM. CO., LTD., Hwaseong-si, Gyeonggi-do (KR)

(72) Inventors: Jung Hyun Cho, Suwon-si (KR); Jin Cheul Kim, Seoul (KR); Yong Il Kim, Suwon-si (KR); Seung Jun Lee, Gunpo-si (KR); Jae Hyun Park, Suwon-si (KR); Jong Soo Woo, Suwon-si (KR)

(73) Assignee: HANMI PHARM. CO., LTD., Hwaseong-si, Gyeonggi-do (KR)

( * ) Notice: Subject to any disclaimer, the term of this patent is extended or adjusted under 35 U.S.C. 154(b) by 0 days.

(21) Appl. No.: 15/108,940

(22) PCT Filed: Dec. 30, 2014

(86) PCT No.: PCT/KR2014/013087
§ 371 (c)(1),
(2) Date: Jun. 29, 2016

(87) PCT Pub. No.: WO2015/102400
PCT Pub. Date: Jul. 9, 2015

(65) Prior Publication Data
US 2016/0346213 A1    Dec. 1, 2016

(30) Foreign Application Priority Data

Dec. 30, 2013  (KR) .................. 10-2013-0167156
Jun. 11, 2014  (KR) .................. 10-2014-0071081

(51) Int. Cl.
| | |
|---|---|
| *A61K 9/20* | (2006.01) |
| *A61K 9/24* | (2006.01) |
| *A61K 31/397* | (2006.01) |
| *A61K 31/505* | (2006.01) |
| *A61K 9/00* | (2006.01) |
| *A61K 9/48* | (2006.01) |

(52) U.S. Cl.
CPC .......... *A61K 9/2009* (2013.01); *A61K 9/0053* (2013.01); *A61K 9/209* (2013.01); *A61K 9/2013* (2013.01); *A61K 9/2018* (2013.01); *A61K 9/2027* (2013.01); *A61K 9/2054* (2013.01); *A61K 9/2077* (2013.01); *A61K 9/2095* (2013.01); *A61K 9/485* (2013.01); *A61K 9/4833* (2013.01); *A61K 9/4858* (2013.01); *A61K 9/4866* (2013.01); *A61K 31/397* (2013.01); *A61K 31/505* (2013.01)

(58) Field of Classification Search
None
See application file for complete search history.

(56) References Cited

U.S. PATENT DOCUMENTS

| | | |
|---|---|---|
| 5,260,440 A | 11/1993 | Hirai et al. |
| 5,696,116 A | 12/1997 | Clozel et al. |
| 7,179,792 B2 | 2/2007 | Glombik et al. |
| 9,320,718 B2 * | 4/2016 | Cho ............... A61K 9/4891 |
| 2005/0026992 A1 | 2/2005 | Sasmal et al. |
| 2007/0275052 A1 | 11/2007 | Mahajan et al. |
| 2010/0204195 A1 | 8/2010 | Lulla et al. |
| 2011/0098315 A1 | 4/2011 | Farshi et al. |
| 2011/0196383 A1 | 8/2011 | Aziz et al. |
| 2011/0251187 A1 | 10/2011 | Kasai et al. |
| 2013/0028974 A1 * | 1/2013 | Kim ................ A61K 45/06 424/465 |
| 2013/0190487 A1 | 7/2013 | Stimac et al. |
| 2016/0045444 A1 * | 2/2016 | Kim ................ A61K 9/4891 424/452 |

FOREIGN PATENT DOCUMENTS

| | | |
|---|---|---|
| CN | 101679236 A | 3/2010 |
| EP | 2 229 938 A1 | 9/2010 |
| EP | 2 468 258 A1 | 6/2012 |
| JP | 2010-534644 A | 11/2010 |
| KZ | 6024 B | 4/1998 |
| MX | 2012014970 A | 8/2013 |
| RU | 2 380 093 C2 | 1/2010 |
| WO | 95/08532 A1 | 3/1995 |
| WO | 02/050090 A1 | 6/2002 |
| WO | 02/058732 A2 | 8/2002 |

(Continued)

OTHER PUBLICATIONS

Davis, Jr. et al., "The Synergistic Hypocholesterolemic Activity of the Potent Cholesterol Absorption Inhibitor, Ezetimibe, in Combination With 3-Hydroxy-3-Methylglutaryl Coenzyme A Reductase Inhibitors in Dogs", Metabolism, vol. 50, No. 10, pp. 1234-1241, (2001).

Sudhop et al., "Cholesterol Absorption Inhibitors for the Treatment of Hypercholesterolaemia", Drugs, vol. 62, No. 16, pp. 2333-2347, (2002).

Torimoto et al., "Efficacy of combination of Ezetimibe 10 mg and rosuvastatin 2.5 mg versus rosuvastatin 5 mg monotherapy for hypercholesterolemia in patients with type 2 diabetes", Lipids in Health and Disease, 2013, 12:137, 9 pages.

Cheyushov, Promyshlennaya technologiya lekarstv // Harkov izdatelstvo NFAU. MTK-Kniga. 2002. Tom 2. pp. 353-355.

Khanfar et al., Formulation factors affecting the release of ezetimibe from different liquisolid compacts, Pharmaceutical Development and Technology, 2012, 11 pages.

(Continued)

*Primary Examiner* — David J Blanchard
*Assistant Examiner* — Daniel F. Coughlin
(74) *Attorney, Agent, or Firm* — Vorys, Sater, Seymour & Pease LLP; Mih Suhn Koh (57) ABSTRACT

Provided are a solid composite formulation for oral administration, the solid composite formulation including: an ezetimibe granules-part including ezetimibe, said ezetimibe having a particle size distribution wherein the average particle size d(0.9) for the bottom 90% is about 10 μm or less; and a rosuvastatin mixture-part including rosuvastatin or a pharmaceutically acceptable salt thereof, and a method of preparing the composite formulation.

10 Claims, 4 Drawing Sheets

(56) References Cited

FOREIGN PATENT DOCUMENTS

| WO | 2006/107936 A1 | 10/2006 |
| WO | 2008/060476 A2 | 5/2008 |
| WO | 2008/101723 A2 | 8/2008 |
| WO | 2009/024889 A2 | 2/2009 |
| WO | 2011/019326 A2 | 2/2011 |
| WO | 2011/139256 A2 | 11/2011 |
| WO | 2012/064307 A1 | 5/2012 |
| WO | 2013/066279 A1 | 5/2013 |
| WO | 2013/166117 A1 | 11/2013 |

OTHER PUBLICATIONS

Pre-Grant Opposition as filed by Pharmaceutical Laboratories Association (ALAFAR) against the Ecuador Patent Application No. IEPI-2016-57283, with English Summary, filed Dec. 2018.

* cited by examiner

|  | EXAMPLE 2 | EXAMPLE 4 | COMPARATIVE EXAMPLE 12 | COMPARATIVE EXAMPLE 13 |
|---|---|---|---|---|
| AUC(0~24hr) | 262.1 | 234.5 | 166.5 | 128.8 |
| Cmax(ng/ml) | 55.6 | 51.2 | 48.3 | 38.8 |
| Tmax(hr) | 1.3 | 1.2 | 1.1 | 1.1 |

COMPOSITE FORMULATION FOR ORAL ADMINISTRATION COMPRISING EZETIMIBE AND ROSUVASTATIN

TECHNICAL FIELD

The present disclosure relates to a composite formulation for oral administration having improved stability and dissolution rates of active ingredients including ezetimibe and rosuvastatin or a pharmaceutically acceptable salt thereof, and a method of preparing the composite formulation.

BACKGROUND ART

Rosuvastatin and its pharmaceutically acceptable salts are one of HMG-CoA reductase inhibitors that inhibit the synthesis of cholesterol for the treatment of dyslipidemia. Crestor tablets (i.e., rosuvastatin calcium salts available by AstraZeneca), including rosuvastatin as a main ingredient, have been widely used both domestically and internationally for the treatment of dyslipidemia and dyslipidemia-related disorders. In particular, research has been reporting that rosuvastatin has excellent effects on lowering LDL cholesterol levels in blood and increasing beneficial HDL cholesterol levels in the body, as compared with effects of atorvastatin or simvastatin that is commercially available as a drug using the same mechanisms with rosuvastatin. Accordingly, there is an increasing interest in rosuvastatin formulation.

HMG-CoA reductase inhibitors are generally used in a combination with a therapeutic agent for treating dyslipidemia, the therapeutic agent using a different mechanism from that of the HMG-CoA reductase inhibitors, so that HMG-CoA reductase inhibitors may increase therapeutic effects. Among the combinations, due to good drug interaction between the HMG-CoA reductase inhibitor and ezetimibe, which is a drug inhibiting the re-absorption of cholesterol in the small intestine, a composite formulation consisting of these two ingredients are actively being studied. For example, Vytorin™, which is a composite formulation consisting of simvastatin and ezetimibe, has already demonstrated excellent pharmacological effects and stability thereof, and is currently available in the market with an excellent sales performance.

Rosuvastatin or a pharmaceutically acceptable salt thereof is generally known to be unstable in a strong acidic environment, and thus, is often designed as a pharmaceutical formulation that includes a basic stabilizer. However, in the case of ezetimibe, which is unstable in a strong basic environment, a large number of ezetimibe-related compounds are produced. Furthermore, in a specific basic pH environment, the related compounds are increased by the interaction between ezetimibe and rosuvastatin so significantly that a composite formulation of rosuvastatin and ezetimibe fails to be commercialized. Thus, due to rosuvastatin and ezetimibe having different stable pH conditions from each other, it is not easy to ensure the stability of the active ingredients, i.e., rosuvastatin and ezetimibe, when preparing the composite formulation of rosuvastatin and ezetimibe.

In addition, in order to prepare an effective composite formulation, it is necessary to ensure high bioavailability of the active ingredients. A dissolution pattern of active ingredients of a solid formulation for oral administration is closely related to the bioavailability of the formulation, wherein high dissolution rate is premised on high bioavailability. In general, the smaller the active ingredient particles are in size, the better the dissolution rates thereof are. Smaller particle sizes of the active ingredients increase the surface areas. However, the stability thereof is more likely to be affected by the surrounding environment (refer to WO2010/056039). Therefore, if active ingredients of a composite formulation have different stable pH conditions from each other as in the case of the composite formulation of rosuvastatin and ezetimibe, reduction in particle size may cause an increase in the production of the related compounds within the composite formulation. Thus, it is difficult to expect high dissolution rates by simply reducing the particle size of the active ingredients.

DISCLOSURE OF INVENTION

Technical Problem

The present invention provides a solid composite formulation for oral administration having improved stability and dissolution rates of active ingredients including ezetimibe and rosuvastatin or a pharmaceutically acceptable salt thereof.

The present invention provides a method of preparing the solid composite formulation for oral administration.

Solution to Problem

According to an aspect of the present invention, there is provided a solid composite formulation for oral administration, the solid composite formulation including:

an ezetimibe granules-part including ezetimibe, said ezetimibe having a particle size distribution wherein the average particle size $d_{(0.9)}$ for the bottom 90% is about 10 μm or less; and a rosuvastatin mixture-part including rosuvastatin or a pharmaceutically acceptable salt thereof.

According to another aspect of the present invention, there is provided a solid composite formulation for oral administration, the solid composite formulation including:

an ezetimibe wet granules-part including ezetimibe, said ezetimibe having a particle size distribution wherein the average particle size $d_{(0.9)}$ for the bottom 90% is about 10 μm or less; and a rosuvastatin mixture-part including rosuvastatin or a pharmaceutically acceptable salt thereof, wherein the ezetimibe wet granules-part or the rosuvastatin mixture-part includes, based on 1 part by weight of ezetimibe granules, a diluent in an amount of about 0.5 to about 50 parts by weight, a binder in an amount of about 0.1 to about 20 parts by weight, a disintegrant in an amount of about 0.1 to about 40 parts by weight, a glidant in an amount of about 0.1 to about 3 parts by weight, or any combinations thereof.

According to another aspect of the present invention, there is provided a method of preparing a solid composite formulation for oral administration, the method including:

preparing an ezetimibe granules-part comprising ezetimibe, said ezetimibe having a particle size distribution wherein the average particle size $d_{(0.9)}$ for the bottom 90% is about 10 μm or less; and formulating the ezetimibe granules-part and a rosuvastatin mixture-part including rosuvastatin or a pharmaceutically acceptable salt thereof.

Advantageous Effects of Invention

A composite formulation for oral administration according to the present invention may include active ingredients, i.e., ezetimibe and rosuvastatin or a pharmaceutically acceptable salt thereof, wherein each of the active ingredients is stable and has a high dissolution rate, resulting in high bioavailability. Therefore, the composite formulation for oral administration according to the present invention may improve a patient's compliance, and eventually, may contribute to the effective treatment of dyslipidemia.

MODE FOR THE INVENTION

Unless otherwise defined, all terms (including technical and scientific terms) used herein have the same meaning as commonly understood by one of ordinary skill in the art to which this invention belongs. Although exemplary methods or materials are listed herein, other similar or equivalent ones are also within the scope of the present invention. All publications disclosed as references herein are incorporated in their entirety by reference.

Ezetimibe and rosuvastatin as pharmacologically active ingredients of a composite formulation according to the present invention may suffer from stability problems by an increase in the production of related compounds of ezetimibe and rosuvastatin when formulating a composite formulation of ezetimibe and rosuvastatin having different stable pH conditions from each other. In the case of rosuvastatin, production of related compounds, such as (3R,6E)-7-[4-(4-fluorophenyl)-2-(N-methylmethanesulfonamido)-6-(propane-2-yl)pyrimidine-5-yl]-3-hydroxy-5-oxo-hept-6-enoate calcium (hereinafter, referred to as '5-Oxo-related compound'), and N-[4-(4-fluorophenyl)-6-(1-methylethyl)-5-[(1E)-2-[(2S,4R)tetrahydro-4-hydroxy-6-oxo-2H-pyran-2-yl]ethenyl]-2-pyrimidinyl]-N-methylmethanesulfonamide (hereinafter, referred to as 'lactone-related compound'), which are main metabolites of rosuvastatin, may be increased. The inventors of the present invention, in order to formulate a solid composite formulation for oral administration including ezetimibe and rosuvastatin, included ezetimibe as a separate granules-part and rosuvastatin or a pharmaceutically acceptable salt thereof as a rosuvastatin mixture-part, and adjusted the ezemitibe to have a particle size distribution wherein the average particle size $d_{(0.9)}$ for the bottom 90% is about 10 μm or less, thereby improving dissolution rates and ensuring stability of the composite formulation.

Thus, an aspect of the present invention provides a solid composite formulation for oral administration, the solid composite formulation including:

an ezetimibe granules-part including ezetimibe, said ezetimibe having a particle size distribution wherein the average particle size $d_{(0.9)}$ for the bottom 90% is about 10 μm or less; and a rosuvastatin mixture-part including rosuvastatin or a pharmaceutically acceptable salt thereof.

As used herein, the term "average particle size $d_{(0.9)}$ for the bottom 90%" refers to an average particle size of particles corresponding to 90% of a total number of particles measured from the smallest particles by using an apparatus for measuring particle size, and hereinafter, the term is referred to as "particle size $d_{(0.9)}$," in short.

The ezetimibe included as a first pharmacologically active ingredient may have a particle size $d_{(0.9)}$ of about 10 μm or less, specifically, about 7.5 μm or less. In some embodiments, the particle size $d_{(0.9)}$ of ezetimibe may be in a range of about 0.8 μm to about 10 μm. Here, ezetimibe having a particle size $d_{(0.9)}$ of less than 0.8 μm may not be easily prepared.

When the particle size $d_{(0.9)}$ of ezetimibe is greater than 10 μm, dissolution rates of ezetimibe are found to be significantly reduced. In the related art, when the particle size of the active ingredients of the composite formulation of ezetimibe and rosuvastatin is reduced due to different stable pH conditions of the active ingredients, the interaction of the active ingredients in the surrounding condition is increased, and accordingly, there is a concern for the stability of the active ingredients in the composite formulation being decreased. In the present invention, the dissolution rate of ezetimibe is found to be significantly increased in a case where the particle size $d_{(0.9)}$ of the active ingredient, i.e., ezetimibe, is reduced to 10 μm or less, as compared with a case where the particle size $d_{(0.9)}$ of ezetimibe is greater than about 10 μm (refer to Experimental Examples 5 and 6). In addition, as a result of actual administration of the composite formulation according to the present invention to adults, the bioavailability of the active ingredient, i.e., ezetimibe, is found to be significantly increased in the case where the particle size $d_{(0.9)}$ of ezetimibe is about 10 μm or less, as compared with the case where the particle size $d_{(0.9)}$ of ezetimibe is greater than about 10 μm (refer to Experimental Example 8). According to the results that the dissolution rate of ezetimibe rather than ezetimibe-related compounds is significantly increased, it is found that the dissolution rate of ezetimibe may be increased without a concern for the decrease in stability, which may be caused by reduction in the particle size. Thus, the solid composite formulation for oral administration according to the present invention may have unexpected effects in terms of solving the concern for the expected, reduced stability caused by reducing the particle size of the active ingredients due to them having different stable pH conditions from each other. In addition, it is found that the increase in the stability and the dissolution rates of the active ingredients leads to the increase in the bioavailability of the active ingredients upon actual administration of the composite formulation of the present invention to a human, thereby obtaining a practically effective composite formulation.

The composite formulation according to the present invention may include ezetimibe at about 5 mg to about 20 mg in a unit dosage form, and in some embodiments, at about 5 mg to about 10 mg in a unit dosage form.

The composite formulation according to the present invention may include the ezetimibe granules-part in a wet granules form. According to an experimental example, the composite formulation including ezetimibe in a wet granules form is shown to have low production of the ezetimibe-related compounds and excellent tableting characteristics, as compared with the composite formulation including ezetimibe in a non-wet granules form (refer to Experimental Example 4).

As used herein, the term "wet granules-part" refers to mixed granules prepared in a wet state, and the term "mixture-part" refers to a mixture of ingredients in a non-granular form.

The composite formulation according to the present invention includes rosuvastatin or a pharmaceutically acceptable salt thereof as a second pharmacologically active ingredient.

Rosuvastatin may be in the form of a free base or in a pharmaceutically acceptable salt thereof. Examples of the pharmaceutically acceptable salt include a calcium salt, a magnesium salt, and a strontium salt, and in an embodiment, a rosuvastatin calcium salt, but the pharmaceutically acceptable salt is not limited thereto.

Rosuvastatin or a pharmaceutically acceptable salt thereof may inhibit an HMG-CoA reductase, which is an essentially required for the synthesis of cholesterol, so as to lower LDL-cholesterol levels in blood and raise HDL-cholesterol levels in blood, thereby contributing to the treatment of dyslipidemia.

The composite formulation according to the present invention may include rosuvastatin or a pharmaceutically acceptable salt thereof at about 2.5 mg to about 40 mg in a unit dosage form, and in some embodiments, at about 5 mg to about 20 mg in a unit dosage unit.

The composite formulation according to the present invention may further include, in addition to the pharmacologically active ingredient, at least one pharmaceutically acceptable additive. In detail, the composite formulation according to the present invention may include at least one of the pharmaceutically acceptable additives selected from the group consisting of a diluent, a binder, a disintegrant, and a glidant.

Another aspect of the present invention provides a solid composite formulation for oral administration including:

an ezetimibe wet granules-part including ezetimibe, said ezetimibe having a particle size distribution wherein the average particle size $d_{(0.9)}$ for the bottom 90% is about 10 μm or less; and a rosuvastatin mixture-part including rosuvastatin or a pharmaceutically acceptable salt thereof, wherein the ezetimibe wet granules-part or the rosuvastatin mixture-part includes, based on 1 part by weight of ezetimibe granules, a diluent in an amount of about 0.5 to about 50 parts by weight, a binder in an amount of about 0.1 to about 20 parts by weight, a disintegrant in an amount of about 0.1 to about 40 parts by weight, a glidant in an amount of about 0.1 to about 3 parts by weight, or any combinations thereof.

The detailed description above of the one aspect of the present invention may be applied to these wet granules-part and the rosuvastatin mixture-part.

The diluent, the binder, the disintegrant, and the glidant may include any material available as an additive in the art. In some embodiments, the stability and the dissolution rates of the active ingredients may be further improved by appropriately selecting specific additives (refer to Experimental Example 7).

For example, the diluent may be selected from the group consisting of lactose, starch, mannitol, microcrystalline cellulose, carboxymethyl cellulose, and any combinations thereof, but is not limited thereto. For example, the binder may be selected from the group consisting of povidone, hypromellose, hydroxypropyl cellulose, copovidone, and any combinations thereof, but is not limited thereto. For example, the disintegrant may be selected from the group consisting of crospovidone, croscarmellose sodium, sodium starch glycolate, low-substituted hydroxypropyl cellulose, and any combinations thereof, but is not limited thereto. For example, the glidant may be selected from the group consisting of magnesium stearate, talc, light anhydrous silicic acid, sodium stearyl fumarate, and any combinations thereof, but is not limited thereto.

In some embodiments, the ezetimibe wet granules-part or the rosuvastatin mixture-part may include, based on 1 part by weight of ezetimibe granules, the diluent in an amount of about 0.5 to about 50 parts by weight, the binder in an amount of about 0.1 to about 20 parts by weight, the disintegrant in an amount of about 0.1 to about 40 parts by weight, and the glidant in an amount of about 0.1 to about 3 parts by weight.

In some embodiments, the rosuvastatin mixture-part may further include a weakly basic stabilizer.

As used herein, the term "weakly basic stabilizer" refers to any material available as a basifying agent of which a $pK_b$ value is in a range of about 9 to about 11, and the weakly basic stabilizer may be selected from the group consisting of sodium hydrogen carbonate, potassium hydrogen carbonate, calcium hydrogen carbonate, magnesium hydrogen carbonate, ammonium hydrogen carbonate, and any combinations thereof, but is not limited thereto. For example, the basic stabilizer may be sodium hydrogen carbonate.

The weakly basic stabilizer decreases the proportions of main metabolites of rosuvastatin, i.e., 5-Oxo-related compound and lactone-related compound, so that the stability of rosuvastatin or a pharmaceutically acceptable salt thereof may be improved. At the same time, the stability of ezetimibe, which is unstable in a basic environment, may be also guaranteed.

The amount of the sodium hydrogen carbonate used herein may be in a range of about 0.05 to about 0.5 parts by weight based on 1 part by weight of rosuvastatin. Surprisingly, when the amount of the sodium hydrogen carbonate is in a range of about 0.05 to about 0.5 parts by weight based on 1 part by weight of rosuvastatin, it is found that the amount of related compounds of rosuvastatin or a pharmaceutically acceptable salt thereof, each of which is stable in a basic environment, and ezetimibe, which is stable in an acidic or weakly basic environment, are reduced (refer to Experimental Examples 2 and 3).

As used herein, the term 'solid composite formulation for oral administration' refers to a formulation prepared by molding or encapsulating drugs to a predetermined shape. The solid composite formulation for oral administration according to the present invention may be formulated as a pellet, a capsule, a tablet (including a single-layered tablet, a double-layered tablet, and a pressed core tablet), powders, or granules, but the examples of the solid composite formulation are not limited thereto. For example, the solid composite formulation for oral administration may be in the form of a capsule, a single-layered tablet, or a double-layered tablet form. When the composite formulation according to the present invention is in the form of a capsule, the capsule may be prepared in a form containing powders, granules, tablets, syrup, or pellets within the capsule.

According to an embodiment, the composite formulation of the present invention may show excellent stability thereof based on rosuvastatin-related compounds such as (3R,6E)-7-[4-(4-fluorophenyl)-2-(N-methylmethanesulfonamido)-6-(propane-2-yl)pyrimidine-5-yl]-3-hydroxy-5-oxo-hept-6-enoate calcium or N-[4-(4-fluorophenyl)-6-(1-methylethyl)-5-[(1E)-2-[(2S,4R)tetrahydro-4-hydroxy-6-oxo-2H-pyran-2-yl]ethenyl]-2-pyrimidinyl]-N-methylmethanesulfonamide, produced in an amount of less than 1.0%, or rosuvastatin-related compounds produced in a total amount of less than about 2.0%, for example, less than about 1.0%, during long-term storage for 24 months under conditions of a temperature of about 25° C. and a relative humidity of about 60%. The composite formulation of the present invention may also show excellent stability thereof based on ezetimibe-related compounds produced in a total amount of less than about 1.0%, during long-term storage for 24 months under conditions of a temperature of about 25° C. and a relative humidity of about 60% (refer to Experimental Example 4).

According to an embodiment, ezetimibe dissolution rates of the composite formulation of the present invention may be about 85% or more in 15 minutes, according to a dissolution test method using Dissolution method II in the Korean Pharmacopoeia at a paddle rotation speed of about 50 rpm with respect to a buffer solution of pH 4.5 containing 0.45% sodium lauryl sulfate. In addition, the composite formulation of the present invention, according to a dissolution test method using Dissolution method II in the Korean Pharmacopoeia at a paddle rotation speed of about 50 rpm with respect to an acetic acid buffer solution of pH 4.0 that does not contain sodium lauryl sulfate, shows significantly excellent ezetimibe dissolution rates, as compared with ezetimibe dissolution rates of other formulations in which the average particle size $d_{(0.9)}$ of ezetimibe particles for the bottom 90% is about 10 μm or greater (refer to Experimental Examples 5 and 6). Therefore, the composite formulation of the present invention is expected to have high bioavailability based on the increased dissolution rates (refer to Experimental Example 8).

According to another aspect of the present invention, there is provided a method of preparing a solid composite formulation for oral administration, the method including: preparing an ezetimibe granules-part comprising ezetimibe, said ezetimibe having a particle size distribution wherein the average particle size $d_{(0.9)}$ for the bottom 90% is about 10 μm or less; and formulating the ezetimibe granules-part and a rosuvastatin mixture-part together, wherein the rosuvastatin mixture-part includes rosuvastatin or a pharmaceutically acceptable salt thereof.

The detailed description above of a solid composite formulation for oral administration according to the any aspects of the present invention may be applied to this method of preparing a solid composite formulation for oral administration.

In an embodiment, the ezetimibe granules-part may be prepared by wet granulation according to the method of the present invention. The wet granulation is not specifically limited, and may be any wet granulation known in the art.

In an embodiment, the ezetimibe granules-part and the rosuvastatin mixture-part according to the method of the present invention may each include, based on 1 part by weight of ezetimibe, a diluent in an amount of about 0.5 to about 50 parts by weight, a binder in an amount of about 0.1 to about 20 parts by weight, a disintegrant in an amount of about 0.1 to about 40 parts by weight, a glidant in an amount of about 0.1 to about 3 parts by weight, or any combinations thereof.

In an embodiment, a method of preparing a composite formulation, according to any of the above-described embodiments, may include:

(i) preparing a wet granules-part comprising ezetimibe according to wet granulation, said ezetimibe having a particle size distribution wherein the average particle size $d_{(0.9)}$ for the bottom 90% is about 10 μm or less;

(ii) preparing a rosuvastatin mixture-part including rosuvastatin or a pharmaceutically acceptable salt thereof; and (iii) mixing the wet granules-part of step (i) and the mixture-part of step (ii) and preparing a single-layered tablet according to a common table preparation method.

In an embodiment, a method of preparing a composite formulation, according to any of the above-described embodiments, may include:

(i) preparing a wet granules-part comprising ezetimibe according to wet granulation, said ezetimibe having a particle size distribution wherein the average particle size $d_{(0.9)}$ for the bottom 90% is about 10 μm or less, and then, tableting the wet granules-part to produce a tablet;

(ii) preparing a rosuvastatin mixture-part including rosuvastatin or a pharmaceutically acceptable salt thereof; and (iii) preparing a double-layered tablet including a first layer of the tablet produced in step (i) and a second layer of the mixture-part of step (ii) by using a tableting machine for double-layered tablets according to a common double-layered tablet preparation method.

In some other embodiments, a method of preparing a composite formulation, according to any of the above-described embodiments, may include:

(i) preparing a wet granules-part comprising ezetimibe according to wet granulation, said ezetimibe having a particle size distribution wherein the average particle size $d_{(0.9)}$ for the bottom 90% is about 10 μm or less;

(ii) adding a rosuvastatin mixture-part including rosuvastatin or a pharmaceutically acceptable salt thereof to the wet granules-part produced in step (i); and (iii) filling a capsule with the mixture of the wet granules-part and the rosuvastatin mixture-part to formulate the composite formulation as a capsule according to a common capsule preparation method.

EXAMPLE

Hereafter, one or more embodiments of the present invention will be described in detail with reference to the following examples. However, these examples are not intended to limit the scope of the one or more embodiments of the present invention.

Preparation Examples 1 to 3 and Comparative Examples 1 to 8: Preparation of Tablets for Identifying Interaction Between the Active Ingredients and Interaction Between Active Ingredients and Basic Stabilizer Constitutional ingredients were mixed according to the ingredients and their amounts as shown in Table 1 below to form mixtures, and the mixtures were compressed according to a disc method under items of 'ultraviolet (UV)-absorption spectrophotometry' in the Korean Pharmacopoeia, thereby preparing discs each in the form of a tablet. Providers of the respective constitutional ingredients are as follows:

Calcium carbonate (Bihoku Funka Kogyo, Japan), magnesium carbonate (Tomita, Japan), and sodium hydrogen carbonate (Penrice soda, Australia).

TABLE 1

| (Unit: mg) | Rosuvastatin calcium salt | Ezetimibe | Calcium carbonate | Magnesium carbonate | Sodium hydrogen carbonate |
|---|---|---|---|---|---|
| Comparative Example 1 | 20.8 (20 mg as rosuvastatin) | — | — | — | — |
| Comparative Example 2 | — | 10 | — | — | — |
| Comparative Example 3 | 20.8 | 10 | — | — | — |
| Comparative Example 4 | 20.8 | 10 | 2 | — | — |
| Comparative Example 5 | 20.8 | 10 | — | 2 | — |
| Comparative Example 6 | 20.8 | 10 | — | — | 0.02 |
| Preparation Example 1 | 20.8 | 10 | — | — | 1 |
| Preparation Example 2 | 20.8 | 10 | — | — | 2 |
| Preparation Example 3 | 20.8 | 10 | — | — | 10 |
| Comparative Example 7 | 20.8 | 10 | — | — | 20 |
| Comparative Example 8 | 20.8 | 10 | — | — | 30 |

Preparation Example 4: Preparation of Single-Layered Tablet Including Ezetimibe Wet Granules and Rosuvastatin Calcium Salt According to the ingredients and their amounts described in the wet granules-part of Table 2 below, ezetimibe was mixed with lactose (DMV-Fonterra Excipients, New Zealand), microcrystalline cellulose (FMC BioPolymer, USA), croscarmellose sodium (DMV-Fonterra Excipients B.V., Netherlands), and sodium lauryl sulfate (Miwon Commercial Co., Ltd, Korea), in a wet granules-part. Then, the mixture was combined with a binding solution in which about 2 mg of povidone (BASF, USA) was dissolved in about 40 mg of water, dried, and sieved with a mesh size of about 30, thereby preparing an ezetimibe wet granules-part.

In addition, according to the ingredients and their amounts described in the post-mixture-part of Table 2, a post-mixture-part, including a rosuvastatin calcium salt and a sodium hydrogen carbonate, was prepared. Providers of the respective components are as follows:

Mannitol (ROQUETTE, France), crospovidone (ISP, USA), and magnesium stearate (NOF CORPORATION, Japan).

The ezetimibe wet granules-part and the post-mixture-part obtained above were mixed together, and then, formulated as a tablet by using a tableting machine.

TABLE 2

| | Wet granules-part (unit: mg) | | Post-mixture-part (unit: mg) | |
|---|---|---|---|---|
| Preparation Example 4 | Ezetimibe | 10 | Rosuvastatin calcium salt (20 mg of rosuvastatin) | 20.8 |
| | | | Sodium hydrogen carbonate | 2 |
| | Lactose | 40 | Mannitol | 100 |
| | Microcrystalline cellulose | 17 | Microcrystalline cellulose | 45 |
| | Croscarmellose sodium | 5 | Lactose | 110 |
| | Sodium lauryl sulfate | 2 | Crospovidone | 3.5 |
| | Povidone | 2 | Magnesium stearate | 3.5 |

Preparation Example 5: Preparation of Double-Layered Tablet Including Ezetimibe Wet Granules and Rosuvastatin Calcium Salt According to the ingredients and their amounts described in the wet granules-part of Table 3 below, ezetimibe was mixed with lactose, microcrystalline cellulose, croscarmellose sodium, and sodium lauryl sulfate. Then, the mixture was combined with a binding solution in which about 2 mg of povidone (BASF, USA) was dissolved in about 40 mg of water, dried, and sieved with a mesh size of about 30, thereby preparing an ezetimibe wet granules-part. The ezetimibe wet granules-part was mixed with magnesium stearate listed in a first layer of Table 3 below, and then, formulated as a tablet using a first-layered tableting part of a double-layered tableting machine (first-layered tableting part).

According to the ingredients and their amounts listed in a second layer of Table 3 below, a second-layered mixture-part including a rosuvastatin calcium salt was prepared, and then, formulated as a double-layered tablet consisting of a first-layered tableting part as a first layer and a second-layered mixture-part as a second layer.

TABLE 3

| | First layer (unit: mg) | | Second layer (unit: mg) | |
|---|---|---|---|---|
| Preparation Example 5 | Wet granules-part | Ezetimibe | 10 | Rosuvastatin calcium salt | 20.8 |
| | | | | Sodium hydrogen carbonate | 2 |
| | | Lactose | 40 | Mannitol | 100 |
| | | Microcrystalline cellulose | 17 | Microcrystalline cellulose | 45 |
| | | Croscarmellose sodium | 5 | Lactose | 110 |

TABLE 3-continued

| | First layer (unit: mg) | | Second layer (unit: mg) | |
|---|---|---|---|---|
| | Sodium lauryl sulfate | 2 | Crospovidone | 3.5 |
| | Povidone | 2 | Magnesium stearate | 2.5 |
| Magnesium stearate | 1 | | | |

Preparation Example 6: Preparation of Capsules Including Ezetimibe Wet Granules and Rosuvastatin Calcium Salt According to the ingredients and their amount of the wet granules-part as shown in Table 4 below, ezetimibe was mixed with lactose, microcrystalline cellulose, croscarmellose sodium, and sodium lauryl sulfate. Then, the mixture was combined with a binding solution in which about 2 mg of povidone (BASF, USA) was dissolved in about 40 mg of water, dried, and sieved with a mesh size of about 30, thereby preparing an ezetimibe wet granules-part.

The ezetimibe wet granules-part was mixed with a post-mixture-part according to ingredients and their amounts of the post-mixture part as shown in Table 4 below, and then, a gelatin capsule 'size 1' (Suheung Capsule Co., Ltd) was filled with the mixture obtained therefrom.

TABLE 4

| | Wet granules-part (unit: mg) | | Post-mixture-part (unit: mg) | |
|---|---|---|---|---|
| Preparation Example 6 | Ezetimibe | 10 | Rosuvastatin calcium salt | 20.8 |
| | | | Sodium hydrogen carbonate | 2 |
| | Lactose | 40 | Mannitol | 100 |
| | Microcrystalline cellulose | 17 | Microcrystalline cellulose | 45 |
| | Croscarmellose sodium | 5 | Lactose | 110 |
| | Sodium lauryl sulfate | 2 | Crospovidone | 3.5 |
| | Povidone | 2 | Magnesium stearate | 3.5 |

Preparation Example 7: Preparation of Single-Layered Tablets Including Ezetimibe Dry Granules and Rosuvastatin Calcium Salts According to the ingredients and their amounts as shown in the dry granules-part of Table 5 below, ezetimibe was mixed with lactose, microcrystalline cellulose, croscarmellose sodium, sodium lauryl sulfate, and povidone, and the mixture was subjected to dry granulation by using a roller compactor (Sejong, South Korea), and then, sieved with a mesh size of about 30, thereby preparing an ezetimibe dry granules-part.

The ezetimibe dry granules-part was mixed with a post-mixture part according to the ingredients and their amounts as shown in a post-mixture-part of Table 5 below, and then, pressed into a tablet by using a tableting machine.

TABLE 5

| | Dry granules-part (unit: mg) | | Post-mixture-part (unit: mg) | |
|---|---|---|---|---|
| Preparation Example 7 | Ezetimibe | 10 | Rosuvastatin calcium salt (20 mg of rosuvastatin) | 20.8 |
| | | | Sodium hydrogen carbonate | 2 |
| | Lactose | 40 | Mannitol | 100 |
| | Microcrystalline cellulose | 17 | Microcrystalline cellulose | 45 |
| | Croscarmellose sodium | 5 | Lactose | 110 |
| | Sodium lauryl sulfate | 2 | Crospovidone | 3.5 |
| | Povidone | 2 | Magnesium stearate | 3.5 |

Comparative Example 9: Preparation of Single-Layered Tablets Including Non-Wet Ezetimibe and Rosuvastatin Calcium Salt According to the ingredients and their amounts as shown in Table 6 below, ezetimibe was mixed with lactose, microcrystalline cellulose, croscarmellose sodium, sodium lauryl sulfate, rosuvastatin calcium salts, sodium hydrogen carbonate, mannitol, crospovidone, and magnesium stearate. The mixture was then sieved with a mesh size of about 30, and thereafter pressed into a tablet using a tableting machine.

TABLE 6

| | Ingredient | Amount (unit: mg) |
|---|---|---|
| Comparative Example 9 | Ezetimibe | 10 |
| | Lactose | 150 |
| | Microcrystalline cellulose | 62 |
| | Croscarmellose sodium | 5 |
| | Sodium lauryl sulfate | 2 |
| | Rosuvastatin calcium salts | 20.8 |
| | Sodium hydrogen carbonate | 2 |
| | Mannitol | 100 |
| | Crospovidone | 3.5 |
| | Magnesium stearate | 3.5 |

Comparative Example 10: Preparation of Capsules Including Non-Wet Ezetimibe and Rosuvastatin Calcium Salt According to the ingredients and their amount as shown in Table 7 below, ezetimibe was mixed with lactose, microcrystalline cellulose, croscarmellose sodium, sodium lauryl sulfate, rosuvastatin calcium salts, sodium hydrogen carbonate, mannitol, crospovidone, and magnesium stearate. Then, a gelatin capsule 'size 1' was filled with the mixture obtained therefrom.

TABLE 7

| | Ingredient | Amount (unit: mg) |
|---|---|---|
| Comparative Example 10 | Ezetimibe | 10 |
| | Lactose | 150 |
| | Microcrystalline cellulose | 62 |
| | Croscarmellose sodium | 5 |
| | Sodium lauryl sulfate | 2 |
| | Rosuvastatin calcium salt | 20.8 |
| | Sodium hydrogen carbonate | 2 |
| | Mannitol | 100 |

TABLE 7-continued

| Ingredient | Amount (unit: mg) |
| --- | --- |
| Crospovidone | 3.5 |
| Magnesium stearate | 3.5 |

Examples 1 to 4 and Comparative Examples 11 to 13: Preparation of Single-Layered Tablets Including Ezetimibe with Various Particle Sizes and Rosuvastatin Calcium Salt Single-layered tablets of Examples 1 to 3 and Comparative Examples 11 to 13 were prepared in the same manner as in Preparation Example 4, and a single-layered tablet of Example 4 was prepared in the same manner as in Preparation Example 7, according to the ingredients and their amounts including ezetimibe in various particle sizes as shown in Table 8 below. Here, ezetimibe used in Example 1 had a particle size of about 1 μm, which is easily available in the art.

TABLE 8

| | Ezetimibe $-d_{(0.9)}$ | Wet and dry granules-part (unit: mg) | | Post-mixture-part (unit: mg) | |
| --- | --- | --- | --- | --- | --- |
| Example 1 | about 0.8 μm | Ezetimibe | 10 | Rosuvastatin calcium salts | 20.8 |
| Example 2 | about 7.5 μm | Lactose | 40 | Sodium hydrogen carbonate | 2 |
| Example 3 | About 10.0 μm | Microcrystalline cellulose | 17 | Mannitol | 10 |
| Example 4 | About 7.5 μm | Croscarmellose sodium | 5 | Microcrystalline cellulose | 45 |
| Comparative Example 11 | About 12.5 μm | Sodium lauryl sulfate | 2 | Lactose | 110 |
| Comparative Example 12 | About 17.0 μm | Povidone | 2 | Crospovidone | 3.5 |
| Comparative Example 13 | About 25.8 μm | | | Magnesium stearate | 3.5 |

Experimental Example 1: Forced Degradation Test of Ezetimibe

The main ingredient, ezetimibe was precisely weighed to about 100 mg and put in a 200 mL volumetric flask. Then, about 20 mL of 90% (v/v) acetonitrile (ACN) was added thereto, and then, completely dissolved by performing ultrasonic extraction for about 10 minutes. Next, the resultant mixture was subjected to a forced degradation test according to each condition using control, oxidation, a strong base, strong acid, and heat as described below.

1) Control: About 10 mL of distilled water was added to the mixture, and the mixture was left in an oven at a temperature of about 60° C. for about 2 hours to proceed a reaction, cooled down to room temperature, and 10 mL of distilled water was dropped thereto.

2) Oxidation: About 10 mL of a 0.5% (v/v) hydrogen peroxide solution was added to the mixture, and the mixture was left in an oven at a temperature of about 60° C. for about 2 hours to proceed a reaction, cooled down to room temperature, and 10 mL of distilled water was dropped thereto.

3) Strong base: About 10 mL of 0.1N NaOH was added to the mixture, and the mixture was left in an oven at a temperature of about 60° C. for about 2 hours to proceed a reaction, cooled down to room temperature, and t 10 mL of 0.1N HCl was dropped thereto (neutralization).

4) Strong acid: About 10 mL of 0.1N HCl was added to the mixture, and the mixture was left in an oven at a temperature of about 60° C. for about 2 hours to proceed a reaction, cooled down to room temperature, and about 10 mL of 0.1N NaOH 10 mL was dropped thereto (neutralization).

5) Heat: About 10 mL of distilled water was added to the mixture, and the mixture was left in an oven at a temperature of about 105° C. for about 2 hours to proceed a reaction, cooled down to room temperature, and about 10 mL of distilled water was dropped thereto.

Then, each of the samples obtained from the degradation test was cooled down to room temperature, and an extract solvent (i.e., a mixed solution of about 0.1 ml of 85% phosphate solution and about 1,000 ml of acetonitrile) was added thereto for each condition above, thereby preparing a test liquid in an amount of 200 mL. Then, the test liquid was analyzed by 'HPLC' according to General Tests as set forth in the Korean Pharmacopoeia and calculated according to a 'quantitation testing method' and an 'related compound testing method', and the amounts of ezetimibe and its main degradation products having 1.3 hours of relative retention time (RRT) were calculated as shown in Table 9 below and FIG. 1.

TABLE 9

Amounts of the main ingredients and the main degradation products thereof.

| | Amount of ezetimibe (%) | Amount of main degradation products (%) |
| --- | --- | --- |
| Control | 57.90% | 39.87% |
| Oxidation | 61.06% | 39.67% |
| Strong base | 1.56% | 81.22% |
| Strong acid | 100.31% | 0.31% |
| Heat | 0.21% | 96.51% |

Figure 1:
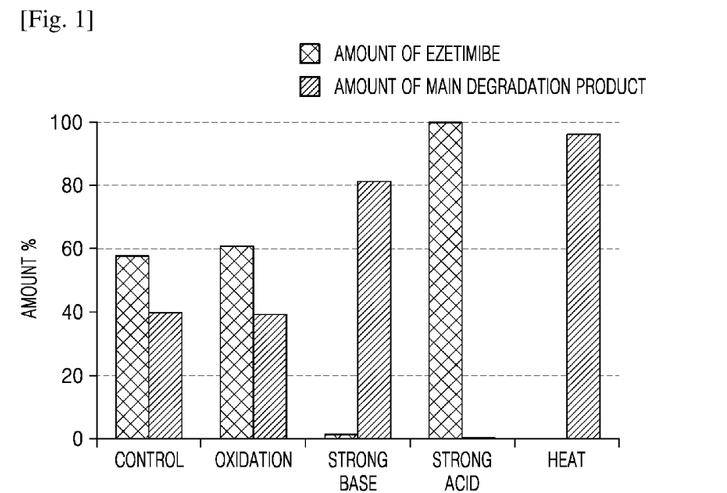
FIG. 1 is a graph showing the amounts of ezetimibe and main degradation products thereof, the amounts being analyzed after performing a forced degradation test on ezetimibe.

Referring to Table 9 and FIG. 1, it was found that ezetimibe was stable under an acidic condition. However, under a neutral or basic pH condition, the speed at which ezetimibe was metabolized to main degradation products was accelerated so that most of ezetimibe was metabolized to degradation products, especially under a strong basic condition. That is, it was found that ezetimibe is degraded under basic conditions and severe heat temperatures.

In addition, the amounts of related compounds of each of the test liquids were calculated, and then, analyzed in connection with an RRT for respective test liquids. The results are shown in Table 10 below.

TABLE 10

Experimental results of related compounds in each test liquid

|  |  | Control | Oxidation | Strong base | Strong acid | Heat |
|---|---|---|---|---|---|---|
| Relative retention time | 0.15 | – | – | + | + | – |
|  | 0.18 | ++ | ++ | +++++ | ++ | ++ |
|  | 0.26 | – | – | + | ++ | – |
|  | 0.47 | +++ | +++ | +++ | – | ++++ |
|  | 0.54 | – | – | +++++ | – | – |
|  | 0.64 | – | – | +++ | – | – |
|  | 0.67 | – | – | ++ | – | – |
|  | 0.74 | – | – | + | – | – |
|  | 1.11 | – | – | + | – | – |
|  | 1.18 | – | – | ++ | – | + |
|  | 1.37 | ++ | ++ | +++++ | – | ++++ |
| Total % |  | 0.63% | 0.61% | 21.48% | 0.45% | 1.97% |

–: Less than 0.05%
+: 0.05% or greater and less than 0.10%
++: 0.10% or greater and less than 0.20%
+++: 0.20% or greater and less than 0.50%
++++: 0.50% or greater and less than 1.0%
+++++: 1.0% or greater Referring to Table 10, it was found that the production of various types of ezetimibe-related compounds increased explosively under a strong basic condition.

In conclusion, based on Tables 9 and 10 and FIG. 1, it was confirmed that ezetimibe was unstable in a basic environment.

Experimental Example 2: Interaction Between Main Ingredients and Interaction Between Rosuvastatin and Basic Stabilizers The discs of Preparation Example 2 and Comparative Examples 1 to 5 were stored for 2 weeks under severe conditions of a temperature of 50° C. and a relative humidity of 75%, and then, finely ground. The amount of ground disc corresponding to 20 mg of rosuvastatin was taken therefrom and put in a 100 mL volumetric flask, and then, was subjected to 'HPLC' analysis for rosuvastatin according to the Korean Pharmacopoeia. The results calculated by the 'related compound testing method' are shown in Table 11 below and FIG. 2.

TABLE 11

Experimental results on related compounds of rosuvastatin

|  | 5-Oxo-related compound | Lactone-related compound | Total related compounds |
|---|---|---|---|
| Comparative Example 1 | 0.01% | 0.45% | 0.49% |
| Comparative Example 2 | — | — | — |
| Comparative Example 3 | 0.51% | 2.13% | 2.97% |
| Comparative Example 4 | 0.01% | 0.22% | 0.25% |
| Comparative Example 5 | 0.02% | 0.18% | 0.21% |
| Preparation Example 2 | 0.01% | 0.19% | 0.21% |

Figure 2:
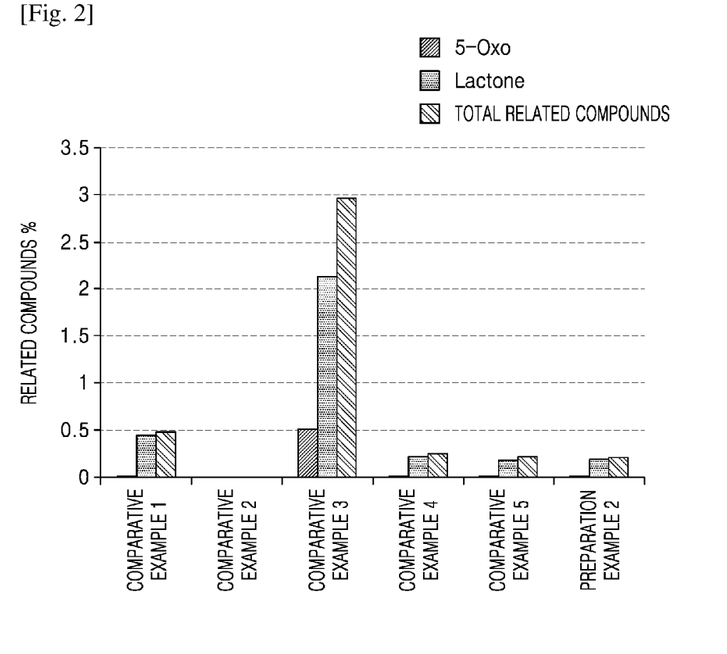
FIGS. 2 and 3 are each a graph showing the amounts of rosuvastatin-related compounds and total ezetimibe-related compounds, the amounts being measured after storing discs of Comparative Examples 1 to 5 and Preparation Example 2 under severe conditions.

Referring to Table 11 and FIG. 2, the interaction between rosuvastatin and ezetimibe exists, and accordingly, it was found that the disc of Comparative Example 3 had increased production of 5-Oxo-related compound and lactone-related compound as main metabolites of rosuvastatin, as compared with the disc of Comparative Example 1. However, in the case of mixing ezetimibe with the basic stabilizers as in Comparative Examples 4 and 5 and Preparation Example 2, it was found that the proportion of the main metabolites of rosuvastatin dramatically decreased.

In addition, the discs of Preparation Example 2 and Comparative Examples 1 to 5, stored and left under severe conditions, were finely ground. The amount of the ground disc corresponding to 100 mg of ezetimibe was taken therefrom, and then, the amount of related compounds was analyzed in the same manner as in Experimental Example 1. The results are shown in Table 12 below and FIG. 3.

TABLE 12

Experimental results on ezetimibe-related compounds

|  | Total related compounds |
|---|---|
| Comparative Example 1 | — |
| Comparative Example 2 | 0.10% |
| Comparative Example 3 | 0.76% |
| Comparative Example 4 | 6.48% |
| Comparative Example 5 | 7.73% |
| Preparation Example 2 | 0.86% |

Figure 3:
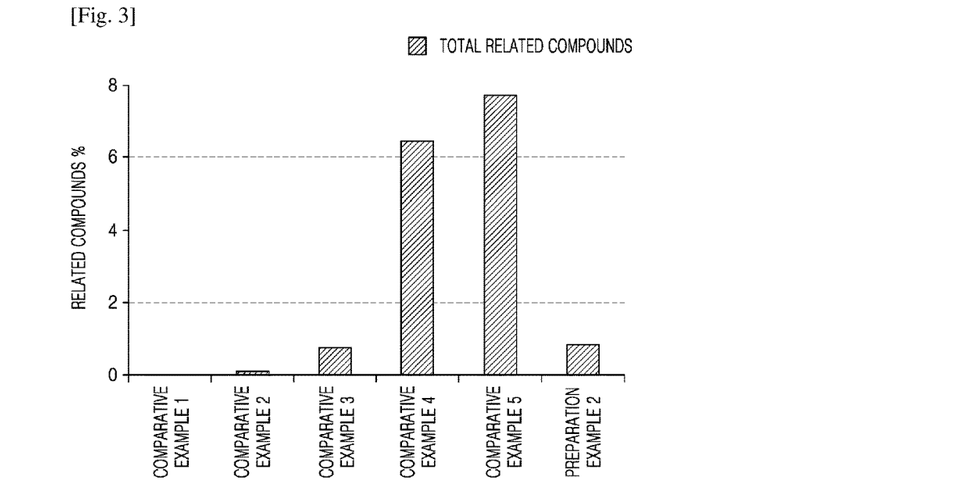

Referring to Table 12 and FIG. 3, the interaction between rosuvastatin and ezetimibe exists, and accordingly, it was found that the disc of Comparative Example 3 had increased production of ezetimibe-related compounds, as compared with the disc of Comparative Example 2. In addition, in the case of mixing ezetimibe with the basic stabilizers as in Comparative Examples 4 and 5, it was confirmed that the production of the total related compounds increased far more than the production of the total related compounds of Comparative Example 3. In the case of Example 2 using sodium hydrogen carbonate as a basic stabilizer, the production of related compounds of Example 2 slightly increased, as compared with that of Comparative Example 3. However, such increase was negligible as compared with that of Comparative Examples 4 and 5 using strongly basic stabilizers.

In conclusion, based on the two results, it is appropriate to use a basic stabilizer in consideration of the stability of rosuvastatin, but in the case of a strongly basic condition, the metabolism speed of ezetimibe increased, thereby affecting a dramatic increase in the production of the related compounds. Thus, it was found that the use of sodium hydrogen carbonate as a weakly basic basifying agent may guarantee the stability of both main ingredients.

Experimental Example 3: Stability Test by Amounts of Sodium Hydrogen Carbonate

In order to find out appropriate amounts of sodium hydrogen carbonate in the composite formulation of the present invention, the discs of Preparation Examples 1 to 3 and Comparative Examples 6 to 8 were each stored for 0, 1, and 2 weeks under severe conditions of a temperature of 50° C. and a relative humidity of 75%. Then, the amounts of rosuvastatin-related compounds were analyzed in the same manner as in Experimental Example 2. The results are shown in Table 13 below and FIG. 4

TABLE 13

Amounts of rosuvastatin-related compounds according to the amount of sodium hydrogen carbonate.

| | 5-Oxo-related compound | | | Lactone-related compound | | | Total related compound | | |
|---|---|---|---|---|---|---|---|---|---|
| | 0 week | 1st week | 2nd week | 0 week | 1st week | 2nd week | 0 week | 1st week | 2nd week |
| Comparative Example 6 | 0.01% | 0.06% | 0.21% | 0.05% | 0.69% | 1.07% | 0.09% | 0.89% | 1.52% |
| Preparation Example 1 | 0.00% | 0.02% | 0.05% | 0.04% | 0.15% | 0.24% | 0.06% | 0.19% | 0.31% |
| Preparation Example 2 | 0.01% | 0.01% | 0.01% | 0.01% | 0.11% | 0.19% | 0.04% | 0.15% | 0.21% |
| Preparation Example 3 | 0.02% | 0.01% | 0.02% | 0.04% | 0.10% | 0.17% | 0.07% | 0.14% | 0.20% |
| Comparative Example 7 | 0.00% | 0.01% | 0.01% | 0.01% | 0.14% | 0.17% | 0.03% | 0.16% | 0.19% |
| Comparative Example 8 | 0.01% | 0.00% | 0.02% | 0.02% | 0.05% | 0.16% | 0.04% | 0.10% | 0.19% |

Figure 4:
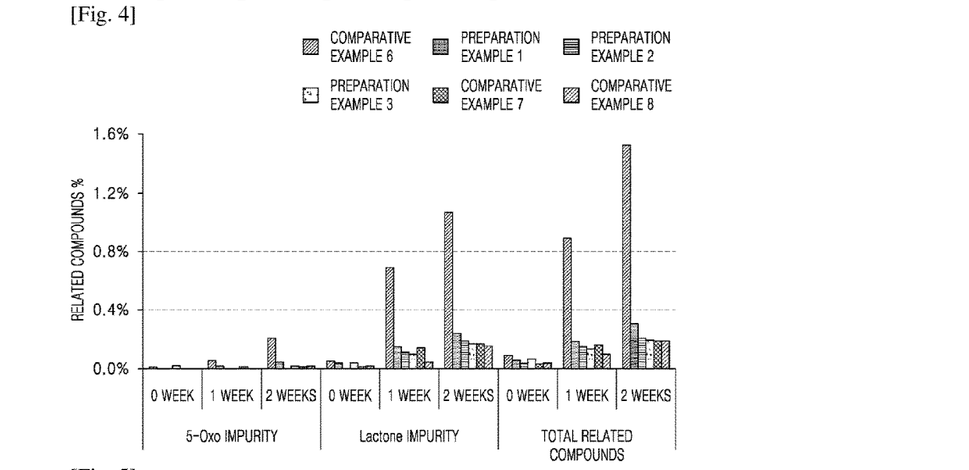
FIGS. 4 and 5 are each a graph showing the amounts of rosuvastatin-related compounds and total ezetimibe-related compounds according to the amounts of hydrogen carbonate in discs of Preparation Examples 1 to 3 and Comparative Examples 6 to 8.

Referring to Table 13 and FIG. 4, it was shown that, as compared with a case where the amount of the sodium hydrogen carbonate was 0.001 part by weight based on 1 part by weight of rosuvastatin as in Comparative Example 6, a case where the amount of the sodium hydrogen carbonate was 0.05 parts by weight or greater based on 1 part by weight of rosuvastatin as in Preparation Examples 1 to 3 and Comparative Examples 7 and 8 significantly decreased the mode of increase in the related compounds.

In addition, the analysis results of the amounts of ezetimibe-related compounds in the discs of Preparation Examples 1 to 3 and Comparative Examples 6 to 8 that were stored under severe conditions above are shown in Table 14 below and FIG. 5.

TABLE 14

Amounts of ezetimibe-related compounds according to the amount of sodium hydrogen carbonate

| | Total related compounds | | |
|---|---|---|---|
| | 0 week | 1st week | 2nd week |
| Comparative Example 6 | 0.07% | 0.32% | 0.75% |
| Preparation Example 1 | 0.02% | 0.45% | 0.79% |
| Preparation Example 2 | 0.04% | 0.44% | 0.86% |
| Preparation Example 3 | 0.03% | 0.57% | 0.94% |
| Comparative Example 7 | 0.05% | 0.64% | 1.01% |
| Comparative Example 8 | 0.04% | 1.77% | 3.20% |

Figure 5:
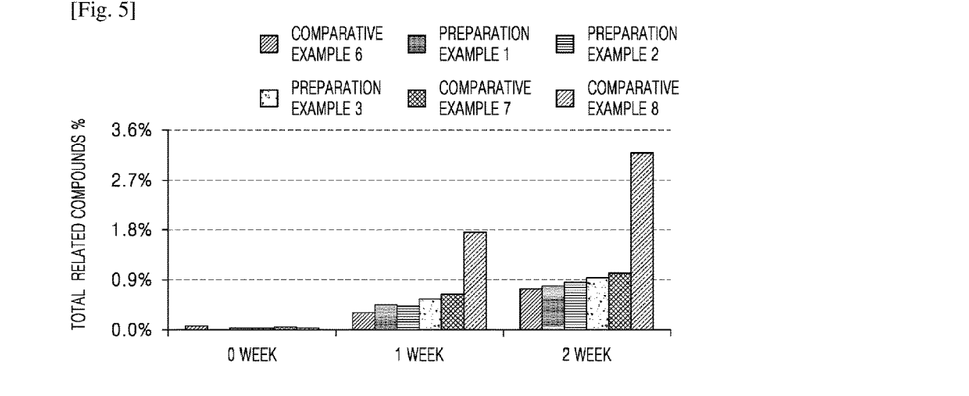

Referring to Table 14 and FIG. 5, it was found that the amounts of the total related compounds in the discs of Comparative Example 6 and Preparation Examples 1 to 3 were about 1.0% or less, which were a significant decrease, as compared with that of the total related compounds in the discs of Comparative Examples 7 and 8.

In conclusion, based on these results, in order to ensure the stability of both main ingredients, rosuvastatin and ezetimibe, at the same time, the amount of the sodium hydrogen carbonate may be appropriately in a range of about 0.05 parts to about 0.5 parts by weight based on 1 part by weight of rosuvastatin.

Experimental Example 4: Stability Test Under Long-Term Conditions

After long-term storage of the tablets and capsules of Preparation Examples 4 to 7 and Comparative Examples 9 and 10, each of which was stored for 0, 6, and 24 months under conditions of a temperature of 25° C. and a relative humidity of 60%, the amounts of rosuvastatin related compounds were analyzed in the same manner as in Experimental Example 2. The results are shown in Table 15 below and FIG. 6.

TABLE 15

Amounts of rosuvastatin-related compounds of composite formulation.

| | 5-Oxo-related compound | | | Lactone-related compound | | | Total related compound | | |
|---|---|---|---|---|---|---|---|---|---|
| | 0 month | 6 months | 24 months | 0 month | 6 months | 24 months | 0 month | 6 months | 0 month |
| Preparation Example 4 | 0.01% | 0.01% | 0.02% | 0.05% | 0.62% | 0.74% | 0.08% | 0.73% | 0.81% |
| Preparation Example 7 | 0.00% | 0.01% | 0.03% | 0.03% | 0.59% | 0.69% | 0.06% | 0.65% | 0.79% |
| Comparative Example 9 | 0.00% | 0.03% | 0.05% | 0.04% | 0.85% | 1.21% | 0.07% | 0.96% | 1.35% |
| Preparation Example 5 | 0.01% | 0.01% | 0.01% | 0.01% | 0.33% | 0.40% | 0.04% | 0.40% | 0.45% |

TABLE 15-continued

Amounts of rosuvastatin-related compounds of composite formulation.

|  | 5-Oxo-related compound | | | Lactone-related compound | | | Total related compound | | |
| --- | --- | --- | --- | --- | --- | --- | --- | --- | --- |
|  | 0 month | 6 months | 24 months | 0 month | 6 months | 24 months | 0 month | 6 months | 0 month |
| Preparation Example 6 | 0.01% | 0.00% | 0.04% | 0.04% | 0.56% | 0.76% | 0.05% | 0.60% | 0.91% |
| Comparative Example 10 | 0.02% | 0.01% | 0.21% | 0.01% | 1.53% | 1.92% | 0.05% | 1.78% | 2.35% |

Figure 6:
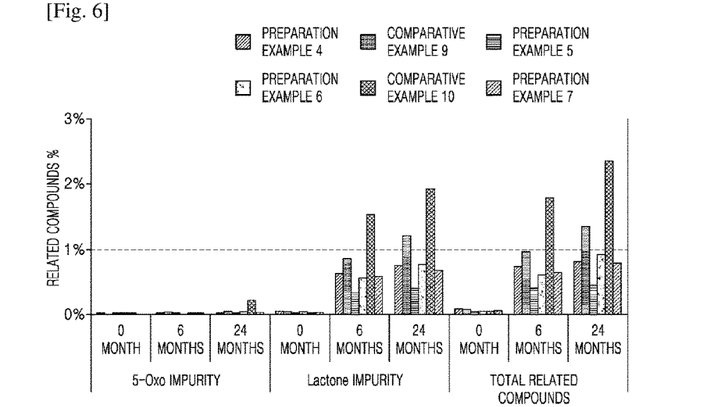
FIGS. 6 and 7 are each a graph showing the amounts of rosuvastatin-related compounds and total ezetimibe-related compounds, the amounts being measured after storing composite formulations of Preparation Examples 4 to 7 and Comparative Examples 9 and 10 for a long period.

Referring to Table 15 and FIG. 6, in terms of long-term stability, a case of including the wet or dry ezetimibe granules as in Preparation Examples 4 to 7 showed a relatively lower increasing of the related compounds regardless of specific types of dosage form, as compared with a case of not including the wet or dry ezetimibe granules as in Comparative Examples 9 and 10. Furthermore, in the case of Examples 4 and 7 which are the single-layered tablets including wet or dry ezetimibe granules, it was found that these single-layered tablets showed dramatically developed tableting characteristics upon the mass production thereof, so that 100,000 tablets (T) or more were possibly produced hourly. In the case of Comparative Example 9 which is the single-layered tablet not including wet or dry ezetimibe granules, it was shown that such single-layered tablet showed low tableting characteristics by which it was possible to produce less than 20,000 tablets (T) hourly in the same apparatus.

Figure 7:
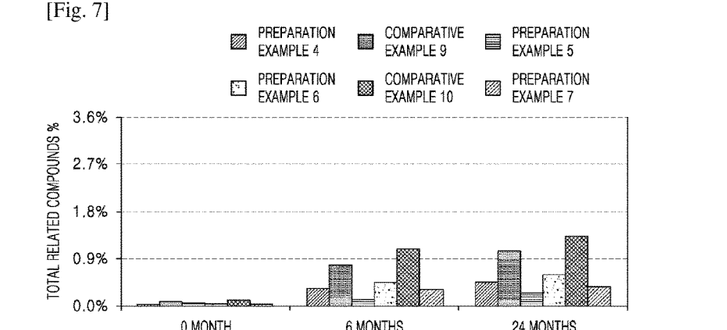

In addition, after long-term storage of the tablets or the capsules of Preparation Examples 4 to 7 and Comparative Examples 9 and 10, the amounts of ezetimibe-related compounds were analyzed, and the results are shown in Table 16 and FIG. 7.

TABLE 16

Amounts of ezetimibe-related compounds of the composite formulation.

|  | Total related compounds | | |
| --- | --- | --- | --- |
|  | 0 month | 6 months | 24 months |
| Preparation Example 4 | 0.01% | 0.32% | 0.44% |
| Preparation Example 7 | 0.02% | 0.35% | 0.41% |
| Comparative Example 9 | 0.07% | 0.78% | 1.04% |
| Preparation Example 5 | 0.06% | 0.13% | 0.25% |
| Preparation Example 6 | 0.03% | 0.44% | 0.59% |
| Comparative Example 10 | 0.10% | 1.08% | 1.32% |

As shown in Table 16 and FIG. 7, Preparation Examples 4 to 7 including wet or dry ezetimibe granules showed significantly lower increasing rate of the related compounds as compared with Comparative Examples 9 and 10 not including wet or dry ezetimibe granules.

In conclusion based on these results, it is expected that the formulation including wet or dry ezetimibe granules has improved its stability due to the least direct contact between ezetimibe and rosuvastatin and the resulting decreased interaction therebetween. In addition, it was confirmed that the physical properties of ezetimibe which is not appropriate for its tableting and the mass production of the tablets were significantly improved through wet granulation.

Experimental Example 5: Dissolution Test According to Ezetimibe Particle Size (1)

The tablets of Examples 1 to 4 and Comparative Examples 11 to 13 were subjected to the dissolution test of ezetimibe according to the following conditions, and the results are shown in Table 17 below and FIG. 8.

<Dissolution Test>
1) Dissolution method: Dissolution method II in the Korean Pharmacopoeia (paddle method)
2) Dissolution medium: 0.45% sodium lauryl sulfate solution (i.e., a well-mixed solution made by dissolving 3.9 g of sodium dihydrogen phosphate in 900 mL of water, adjusting the solution to have pH 4.5 by using 50% (w/w) sodium hydroxide solution or phosphate, and then, adding water thereto to have a total amount of 1,000 mL) in a 0.025M sodium dihydrogen phosphate $NaH_2PO_4.H_2O$ buffer (pH 4.5)
3) Amount of dissolution medium: 500 mL
4) Temperature of dissolution apparatus: 37.5° C.
5) Paddle speed: 50 rpm
6) Number of experimental groups: 6
7) Sample taking time: 0, 5, 10, 15, and 30 minutes

TABLE 17

Results of the dissolution test according to ezetimibe particle size

|  | Example 1 | | Example 2 | | Example 3 | | Example 4 | |
| --- | --- | --- | --- | --- | --- | --- | --- | --- |
| Time (min) | Average | Standard deviation | Average | Standard deviation | Average | Standard deviation | Average | Standard deviation |
| 0 | 0.0 | 0.0 | 0.0 | 0.0 | 0.0 | 0.0 | 0.0 | 0.0 |
| 5 | 70.2 | 6.9 | 43.5 | 10.1 | 38.2 | 5.3 | 39.4 | 7.3 |
| 10 | 93.8 | 3.9 | 85.1 | 3.3 | 81.7 | 2.0 | 80.9 | 3.1 |
| 15 | 96.9 | 2.5 | 92.4 | 1.7 | 90.4 | 2.2 | 90.1 | 2.0 |
| 30 | 97.0 | 1.4 | 95.7 | 1.5 | 94.4 | 1.8 | 94.7 | 1.9 |

|  | Comparative Example 11 | | Comparative Example 12 | | Comparative Example 13 | |
| --- | --- | --- | --- | --- | --- | --- |
| Time (min) | Average | Standard deviation | Average | Standard deviation | Average | Standard deviation |
| 0 | 0.0 | 0.0 | 0.0 | 0.0 | 0.0 | 0.0 |
| 5 | 25.0 | 6.1 | 23.5 | 7.2 | 19.8 | 4.3 |
| 10 | 56.4 | 1.1 | 48.2 | 3.1 | 39.5 | 3.3 |
| 15 | 77.2 | 0.7 | 65.3 | 2.5 | 52.3 | 1.0 |
| 30 | 91.2 | 0.6 | 81.0 | 1.2 | 70.1 | 0.5 |

Figure 8:
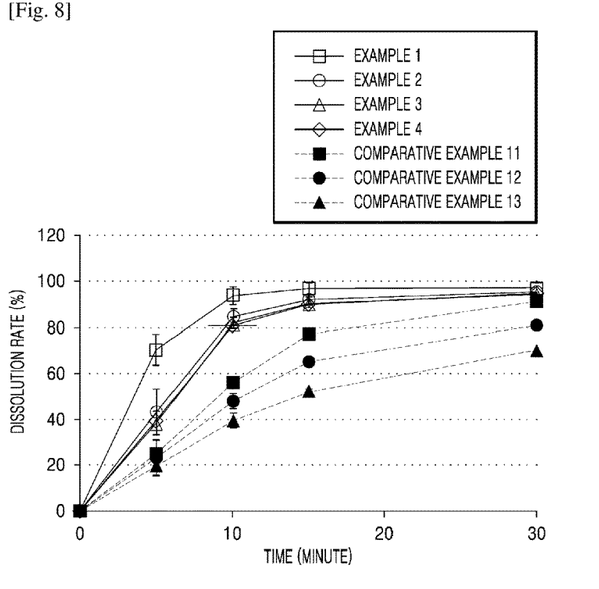
FIG. 8 is a graph showing the results of the dissolution test according to a particle size of ezetimibe, the results being obtained by dissolving tablets of Examples 1 to 4 and Comparative Examples 11 to 13 in a buffer solution of pH 4.5 containing 0.45% sodium lauryl sulfate at a paddle rotation speed of about 50 rpm by using Dissolution method II in the Korean Pharmacopoeia.

Referring to Table 17 and FIG. 8, it was shown that there were significant differences in the dissolution rates of the final composite formulations according to the average particle size for the bottom 90%. In the case of Examples 1 to 4, in which the average particle size for the bottom 90% was about 10.0 μm or less, the composite formulations showed dissolution rates of about 85% or more in 15 minutes, the dissolution rates being significantly improved as compared with those of the composite formulations of Comparative Examples 11 to 13. To guarantee high bioavailability, a pharmaceutical formulation, including ezetimibe, generally needs to have excellent dissolution distribution, and in this regard, these results seem to achieve the purpose of the present disclosure.

Experimental Example 6: Dissolution Test According to Ezetimibe Particle Size (2)

The tablets of Examples 1 to 4 and Comparative Examples 11 to 13 were subjected to the dissolution test of ezetimibe according to the conditions below, and the results are shown in Table 18 below and FIG. 9.

<Dissolution Test>
1) Dissolution method: Dissolution method II in the Korean Pharmacopoeia (paddle method)
2) Dissolution medium: 10 Edition in the Korean Pharmacopoeia, acetic acid of general test method, a sodium acetate buffer of pH 4.0
3) Amount of dissolution medium: 900 mL
4) Temperature of dissolution apparatus: 37.5° C.
5) Paddle speed: 50 rpm
6) Number of experimental groups: 6
7) Sample taking time: 0, 5, 10, 15, 30, 45 and 60 minutes

TABLE 18

Results of the dissolution test according to ezetimibe particle size

| Time (minute) | Example 1 | | Example 2 | | Example 3 | | Example 4 | |
|---|---|---|---|---|---|---|---|---|
| | Average | Standard deviation | Average | Standard deviation | Average | Standard deviation | Average | Standard deviation |
| 5 | 0.467 | 0.200 | 0.433 | 0.111 | 0.411 | 0.167 | 0.419 | 0.155 |
| 10 | 1.111 | 0.078 | 1.022 | 0.056 | 0.933 | 0.122 | 0.946 | 0.094 |
| 15 | 1.322 | 0.044 | 1.211 | 0.033 | 1.133 | 0.044 | 1.153 | 0.035 |
| 30 | 1.311 | 0.033 | 1.222 | 0.044 | 1.167 | 0.056 | 1.197 | 0.051 |
| 45 | 1.322 | 0.033 | 1.189 | 0.022 | 1.156 | 0.044 | 1.173 | 0.039 |
| 60 | 1.300 | 0.022 | 1.156 | 0.011 | 1.167 | 0.033 | 1.159 | 0.018 |

| Time (minute) | Comparative Example 11 | | Comparative Example 12 | | Comparative Example 13 | |
|---|---|---|---|---|---|---|
| | Average | Standard deviation | Average | Standard deviation | Average | Standard deviation |
| 5 | 0.122 | 0.167 | 0.111 | 0.133 | 0.011 | 0.078 |
| 10 | 0.467 | 0.311 | 0.244 | 0.211 | 0.122 | 0.056 |
| 15 | 1.022 | 0.089 | 0.744 | 0.089 | 0.367 | 0.033 |
| 30 | 1.056 | 0.056 | 0.889 | 0.033 | 0.711 | 0.033 |
| 45 | 1.022 | 0.022 | 0.878 | 0.044 | 0.767 | 0.011 |
| 60 | 1.033 | 0.033 | 0.833 | 0.033 | 0.778 | 0.022 |

Figure 9:
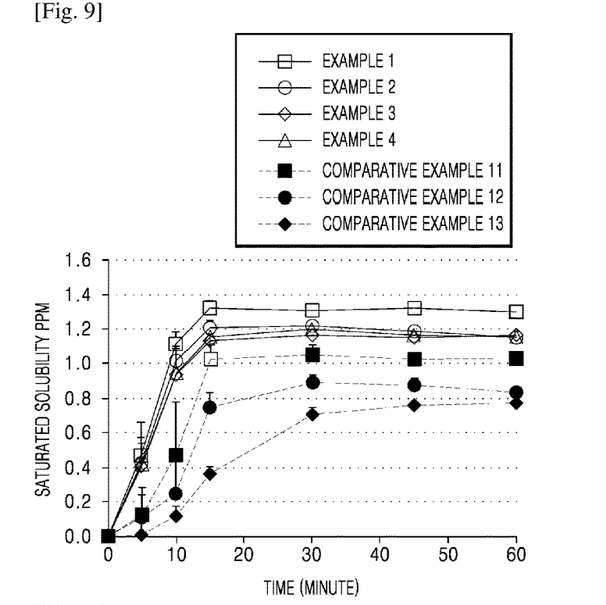
FIG. 9 is a graph showing the results of the dissolution test according to a particle size of ezetimibe, the results being obtained by dissolving tablets of Examples 1 to 4 and Comparative Examples 11 to 13 in a buffer solution of pH 4.0 containing sodium acetate at a paddle rotation speed of about 50 rpm by using Dissolution method II in the Korean Pharmacopoeia.

Referring to Table 18 and FIG. 9, it was confirmed that there were significant differences in the dissolution rates of the final composite formulations according to the average particle size for the bottom 90%. In the case of Examples 1 to 4, in which the average particle size for the bottom 90% was about 10.0 μm or less, the composite formulations showed dissolution rates that were significantly improved as compared with those of the composite formulations of Comparative Examples 11 to 13. In addition, it was shown that the composite formulations of Examples 2 and 4, including ezetimibe of the same particle size, had excellent dissolution rates at a similar level. To guarantee high bioavailability, a pharmaceutical formulation, including ezetimibe, generally needs to have excellent dissolution distribution, and in this regard, these results seem to achieve the purpose of the present disclosure.

Experimental Example 7: Stability Test According to the Presence of Additive The amounts of the total related compounds were measured in tablets that were prepared in the same manner as in Example 3 and Comparative Example 13, except that each of the tablets was prepared by including an additive represented in Table 19 and 20 below. After leaving the prepared tables for 2 weeks under severe conditions of a temperature of 50° C. and a relative humidity of 75%, the amounts of the rosuvastatin-related compounds and the ezetimibe-related compounds were analyzed in the same manner as in Experimental Example 2, thereby measuring the amounts of the total related compounds. The results are shown in Tables 19 and 20 below.

TABLE 19

| Average particle size of ezetimibe d (0.9) (μm) | Ezetimibe (mg) | additives and their amount (mg) | | Total related compounds (%) |
|---|---|---|---|---|
| 10 | 10 | | No additive | 0.09% |
| | | Diluent (100) | Lactose | 0.19% |
| | | | Mannitol | 0.20% |
| | | | Microcrystalline cellulose | 0.13% |
| | | | Starch | 0.44% |
| | | | Carboxylmethyl cellulose | 0.38% |
| | | | Calcium hydrogen phosphate | 4.72% |
| | | | Erythritol | 1.45% |
| | | | Calcium silicate | 2.88% |
| | | Disintegrant (20) | Crospovidone | 0.22% |
| | | | Croscarmellose sodium | 0.16% |
| | | | Low-substituted hydroxypropyl cellulose | 0.27% |
| | | | Calcium alginate | 1.74% |
| | | | Magnesium aluminosillicate | 6.82% |
| | | Binder (10) | Povidone | 0.17% |
| | | | Hypromellose | 0.10% |
| | | | Hydroxypropyl cellulose | 0.25% |
| | | | Copovidone | 0.24% |
| | | | Calcium lactate | 3.04% |
| | | | Calcium lactate | 1.96% |
| | | Glidant (5) | Magnesium stearate | 0.19% |
| | | | Talc | 0.09% |
| | | | Light anhydrous silicic acid | 0.45% |
| | | | Sodium stearyl fumarate | 0.34% |
| | | | Sucrose fatty acid | 1.23% |
| | | | Glyceryl behenate | 2.15% |

TABLE 20

| Average particle size of ezetimibe $d_{(0.9)}$ (μm) | Ezetimibe (mg) | Additives and their amount (mg) | | Total related compounds (%) |
|---|---|---|---|---|
| 25.8 | 10 | | No additive | 0.10% |
| | | Diluent (100) | Lactose | 0.15% |
| | | | Mannitol | 0.23% |
| | | | Microcrystalline cellulose | 0.20% |
| | | | Starch | 0.41% |
| | | | Carboxylmethyl cellulose | 0.40% |
| | | | Calcium hydrogen phosphate | 5.03% |
| | | | Erythritol | 1.27% |
| | | | Calcium silicate | 2.97% |
| | | Disintegrant (20) | Crospovidone | 0.19% |
| | | | Croscamellose sodium | 0.18% |
| | | | Low-substituted hydroxypropyl cellulose | 0.31% |
| | | | Calcium alginate | 2.72% |
| | | | Magnesium aluminosillicate | 6.11% |
| | | Binder (10) | Povidone | 0.12% |
| | | | Hypromellose | 0.10% |
| | | | Hydroxypropyl cellulose | 0.22% |
| | | | Copovidone | 0.26% |
| | | | Calcium lactate | 4.88% |
| | | | Polyethylene oxide | 1.53% |
| | | Glidant (5) | Magnesium stearate | 0.15% |
| | | | Talc | 0.13% |
| | | | Light anhydrous silicic acid | 0.55% |
| | | | Sodium stearyl fumarate | 0.40% |
| | | | Sucrose fatty acid | 2.88% |
| | | | Glyceryl behenate | 4.01% |

According to the results of the experiments above, it was shown that the related compounds were produced less in the composite formulation in which the average particle size for the bottom 90% was about 10.0 μm or less, than in the composite formulation having a significantly larger average particle size of ezetimibe (a case where an additive was not included), even after long-term storage under severe conditions. Therefore, these data support that the composite formulation of the present invention not only had an increased dissolution rate upon the reduction of the particle size, but also guaranteed the stability thereof.

In addition, when the composite formulations were prepared by including various kinds of additives, the composite formulation including ezetimibe having an average particle size for the bottom 90% of 10.0 μm or less showed production of the related compounds lower or production with no significant difference, compared to the composite formulation including ezetimibe having a significantly larger average particle size, even after long-term storage under severe conditions, wherein the both composite formulations used the same additives. When the average particle size of the active ingredient is reduced, its stability is usually lowered by the high possibility of interaction between the active ingredient and its surrounding additives due to an increased surface area of the active ingredient. However, according to the results above, the relationship between the reduced particle size and the increased production of the related compounds was not observed. Therefore, these data support that the composite formulation of the present invention not only had an increased dissolution rate by the reduction of the particle size, but also guaranteed the stability thereof.

In addition, in the case of inclusion of the additives, such as a binder inducing povidone, hypromellose, hydroxypropyl cellulose, or copovidone; a disintegrant including crospovidone, croscamellose sodium, sodium starch glycolate, or low-substituted hydroxypropyl cellulose; a glidant including magnesium stearate, talc, light anhydrous silicic acid, or sodium stearly fumarate, it was shown that production of the related compounds was significantly low as compared with the case of inclusion of other additives.

Therefore, according to these results, it was found that the composite formulation of the present invention is capable of ensuring its stability even in the case of decreasing the particle size of the active ingredient. Furthermore, the stability of the composite formulation of the present invention may be also further improved by the selection of an additive.

Experimental Example 8: Bioavailability Test

In order to confirm whether bioavailability is actually increased according to the increase of dissolution rates, the evaluation of the blood concentration of ezetimibe was carried out with respect to healthy, adult males. Here, tablets of Examples 2 and 4 and Comparative Examples 12 and 13 were used.

The number of test subject was 6 for each group of test samples, and that is, total number of the test subjects was 18. The tablet (10 mg/T) was orally administered in a conventional manner to each of the test subjects who fasted for 14 hours the day before the oral administration. Afterwards, each of the test subjects was allowed to drink 120 ml of water, and during a sampling time for each subject, 2 ml of blood was taken from cephalic veins of the test subjects. The blood sample obtained therefrom was pre-treated according to a conventional pretreatment method of blood samples, and furthermore, was pre-treated by adding beta-glucuronidase to the blood samples in order to sum up the blood concentration of ezetimibe and the concentration of residual ezetimibe metabolites in the blood. The blood concentration of ezetimibe over time after administration was analyzed by using LC/MS. Then, a pharmacokinetic parameter of ezetimibe was analyzed according to the WinNonlin program.

The results are shown in Table 21 below and FIG. 10.

TABLE 21

Results of the bioavailability of ezetimibe according to particle size.

| | Example 2 | | Example 4 | | Comparative Example 12 | | Comparative Example 13 | |
|---|---|---|---|---|---|---|---|---|
| Hour | Average (ng/ml) | Standard deviation | Average (ng/ml) | Standard deviation | Average (ng/ml) | Standard deviation | Average (ng/ml) | Standard deviation |
| 0.00 | 0.0 | 0.0 | 0.0 | 0.0 | 0.0 | 0.0 | 0.0 | 0.0 |
| 0.25 | 11.0 | 9.5 | 9.9 | 5.6 | 8.8 | 6.9 | 11.3 | 2.9 |
| 0.50 | 30.3 | 13.0 | 27.4 | 11.2 | 23.6 | 9.1 | 24.3 | 10.7 |
| 1.00 | 53.5 | 9.9 | 46.9 | 10.2 | 41.6 | 9.9 | 32.1 | 12 |

TABLE 21-continued

Results of the bioavailability of ezetimibe according to particle size.

| Hour | Example 2 | | Example 4 | | Comparative Example 12 | | Comparative Example 13 | |
|---|---|---|---|---|---|---|---|---|
| | Average (ng/ml) | Standard deviation | Average (ng/ml) | Standard deviation | Average (ng/ml) | Standard deviation | Average (ng/ml) | Standard deviation |
| 1.50 | 40.6 | 10.2 | 34.8 | 9.8 | 35.3 | 14.9 | 28.6 | 9.9 |
| 2.00 | 33.5 | 9.3 | 31.8 | 6.9 | 30.8 | 6.9 | 21.1 | 7.2 |
| 4.00 | 25.4 | 7.8 | 21.9 | 7.5 | 19.1 | 7.0 | 16.8 | 7.7 |
| 6.00 | 17.6 | 5.2 | 16.5 | 4.9 | 15.9 | 7.4 | 13.3 | 3.8 |
| 8.00 | 11.0 | 1.4 | 10.2 | 3.0 | 13.3 | 5.1 | 6.9 | 1.1 |
| 24.00 | 9.5 | 1.1 | 8.2 | 1.5 | 6.9 | 1.1 | 4.5 | 0.8 |

Figure 10:
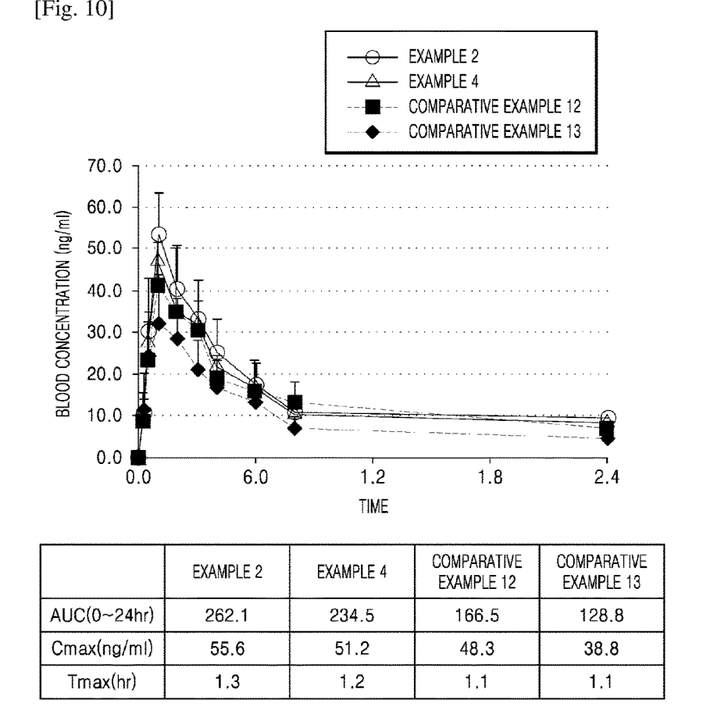
FIG. 10 is a graph showing the results of the bioavailability of tablets of Examples 2 and 4 and Comparative Examples 12 to 13 that are evaluated with respect to adult males according to a particle size of ezetimibe.

Referring to Table 21 and FIG. 10, the composite formulation of Example 2 using ezetimibe that had an average particle size for the bottom of 10.0 µm or less had a significantly high AUC and $C_{max}$ as compared with those of the composite formulations of Comparative Examples 12 and 13 using ezetimibe that had a relatively larger particle size. In particular, the composite formulation of Comparative Example 13 shows half level of the AUC and about 70% of the $C_{max}$ as compared with that of Example 2. Thus, it was confirmed that the particle size of ezetimibe significantly influenced the bioavailability of the composite formulation. In addition, the high dissolution rates were found to actually reflect high bioavailability.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

The invention claimed is:

1. A solid composite formulation for oral administration, the solid composite formulation comprising:
   an ezetimibe granules-part including ezetimibe, said ezetimibe having a particle size distribution wherein the average particle size d(0.9) for the bottom 90% is about 10 µm or less; and
   a rosuvastatin mixture-part including rosuvastatin or a pharmaceutically acceptable salt thereof,
   wherein the rosuvastatin mixture-part further comprises a weak base stabilizer selected from the group consisting of sodium hydrogen carbonate, potassium hydrogen carbonate, magnesium hydrogen carbonate, ammonium hydrogen carbonate, and a combination thereof in an amount of 0.05 parts to 0.5 parts by weight based on 1 part by weight of rosuvastatin,
   wherein the ezetimibe granules-part or the rosuvastatin mixture-part further comprises a diluent selected from the group consisting of lactose, starch, mannitol, microcrystalline cellulose, carboxymethyl cellulose, and a combination thereof; a binder selected from the group consisting of povidone, hypromellose, hydroxypropyl cellulose, copovidone, and a combination thereof; a disintegrant selected from the group consisting of crospovidone, croscarmellose sodium, sodium starch glycolate, low-substituted hydroxypropyl cellulose, and a combination thereof; and/or a glidant selected from the group consisting of magnesium stearate, talc, light anhydrous silicic acid, sodium stearyl fumarate, and a combination thereof.

2. The solid composite formulation of claim 1, wherein the ezetimibe granules-part is a wet granules-part.

3. The solid composite formulation of claim 2, wherein the ezetimibe granules-part or the rosuvastatin mixture-part comprises, based on 1 part by weight of ezetimibe, the diluent in an amount of about 0.5 to about 50 parts by weight, the binder in an amount of about 0.1 to about 20 parts by weight, the disintegrant in an amount of about 0.1 to about 40 parts by weight, the glidant in an amount of about 0.1 to about 3 parts by weight, or a combination thereof.

4. The solid composite formulation of claim 1, wherein the average particle size d(0.9) for the bottom 90% of ezetimibe is in a range of about 0.8 µm to about 10 µm.

5. The solid composite formulation of claim 1, wherein the rosuvastatin mixture-part further comprises sodium hydrogen carbonate in an amount of 0.05 parts to 0.5 parts by weight based on 1 part by weight of rosuvastatin.

6. The solid composite formulation of claim 1, wherein the amount of ezetimibe is in a range of about 5 mg to about 20 mg in a unit dosage form.

7. The solid composite formulation of claim 1, wherein the amount of rosuvastatin or a pharmaceutically acceptable salt thereof is in a range of about 2.5 mg to about 40 mg in a unit dosage form.

8. The solid composite formulation of claim 1, wherein the dissolution rate of ezetimibe is about 85% or more in about 15 minutes when the composite formulation is subjected to a dissolution test at a paddle rotation speed of about 50 rpm in a buffer solution of a pH of about 4.5 containing about 0.45% sodium lauryl sulfate according to Dissolution method II in the Korean Pharmacopoeia.

9. The solid composite formulation of claim 1, wherein (3R,6E)-7-[4-(4-fluorophenyl)-2-(N-methylmethanesulfonamido)-6-(propane-2-yl)pyrimidine-5-yl]-3-hydroxy-5-oxo-hept-6-enoate calcium, or N-[4-(4-fluorophenyl)-6-(1-methylethyl)-5-[(1E)-2-[(2S,4R)tetrahydro-4-hydroxy-6-oxo-2H-pyran-2-yl]ethenyl]-2-pyrimidinyl]-N-methylmethanesulfonamide which is a decomposition product of rosuvastatin, is in an amount of less than 1.0% after long-term storage of the composite formulation for about 24 months under conditions of a temperature of about 25° C. and a relative humidity of about 60%.

10. The solid composite formulation of claim 1, wherein the amount of total decomposition product of ezetimibe is less than about 1.0% after long-term storage of the composite formulation for about 24 months under conditions of a temperature of about 25° C. and a relative humidity of about 60%.

* * * * *